(12) United States Patent
Lipowsky et al.

(10) Patent No.: US 7,323,590 B2
(45) Date of Patent: Jan. 29, 2008

(54) PROCESS FOR RECTIFICATIVELY SEPARATING A LIQUID COMPRISING ACRYLIC ACID AND/OR METHACRYLIC ACID

(75) Inventors: Gunter Lipowsky, Schriesheim (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/400,409

(22) Filed: Apr. 10, 2006

(65) Prior Publication Data

US 2006/0247469 A1    Nov. 2, 2006

Related U.S. Application Data

(60) Provisional application No. 60/675,087, filed on Apr. 27, 2005.

(30) Foreign Application Priority Data

Apr. 27, 2005  (DE) .................... 10 2005 019 911

(51) Int. Cl.
C07C 61/00 (2006.01)

(52) U.S. Cl. ..................................... 562/400

(58) Field of Classification Search ............... None
See application file for complete search history.

(56) References Cited

U.S. PATENT DOCUMENTS

| | | |
|---|---|---|
| 3,932,500 A | 1/1976 | Duembgen et al. |
| 4,113,574 A | 9/1978 | Schumacher et al. |
| 4,496,770 A | 1/1985 | Duembgen et al. |
| 4,828,652 A | 5/1989 | Schropp |
| 5,426,221 A | 6/1995 | Willersinn |
| 5,583,084 A | 12/1996 | Martin et al. |
| 5,739,391 A | 4/1998 | Ruppel et al. |
| 5,780,679 A | 7/1998 | Egly et al. |
| 5,817,865 A | 10/1998 | Machhammer et al. |
| 5,831,124 A | 11/1998 | Machhammer et al. |
| 5,897,749 A | 4/1999 | Kroker et al. |
| 6,166,248 A | 12/2000 | Heida et al. |
| 6,207,022 B1 | 3/2001 | Dockner et al. |
| 6,350,352 B2 | 2/2002 | Kroker et al. |
| 6,350,906 B2 | 2/2002 | Machhammer et al. |
| 6,383,976 B1 | 5/2002 | Arnold et al. |
| 6,413,379 B1 | 7/2002 | Machhammer et al. |
| 6,498,272 B1 | 12/2002 | Schröder et al. |
| 6,596,901 B1 | 7/2003 | Eck et al. |
| 6,646,161 B1 | 11/2003 | Eck et al. |
| 6,679,939 B1 | 1/2004 | Thiel et al. |
| 6,781,017 B2 | 8/2004 | Machhammer et al. |
| 7,119,224 B2 * | 10/2006 | Schroeder et al. ......... 560/205 |
| 2001/0007043 A1 | 7/2001 | Machhammer et al. |
| 2002/0002253 A1 | 1/2002 | Sakamoto et al. |
| 2003/0208093 A1 | 11/2003 | Carlson, Jr. et al. |
| 2004/0054222 A1 | 3/2004 | Felder et al. |
| 2004/0063989 A1 | 4/2004 | Hechler et al. |
| 2004/0181083 A1 | 9/2004 | Proll et al. |
| 2004/0225151 A1 | 11/2004 | Yada et al. |
| 2004/0242826 A1 | 12/2004 | Nishimura |
| 2005/0077240 A1 | 4/2005 | Hofer et al. |
| 2005/0090628 A1 | 4/2005 | Eck et al. |

FOREIGN PATENT DOCUMENTS

| | | |
|---|---|---|
| DE | 54354 | 3/1967 |
| DE | 2 136 396 | 2/1973 |
| DE | 2 207 184 | 8/1973 |
| DE | 43 08 087 A1 | 9/1994 |
| DE | 44 31 949 A1 | 3/1995 |
| DE | 44 05 059 A1 | 8/1995 |
| DE | 44 36 243 A1 | 4/1996 |
| DE | 195 39 295 A1 | 4/1997 |
| DE | 196 06 877 A1 | 8/1997 |
| DE | 196 27 847 A1 | 1/1998 |
| DE | 196 31 645 A1 | 2/1998 |
| DE | 196 34 614 A1 | 3/1998 |
| DE | 197 40 253 A1 | 3/1999 |
| DE | 198 55 913 A1 | 6/2000 |
| DE | 199 24 532 A1 | 11/2000 |
| DE | 199 24 533 A1 | 11/2000 |
| DE | 101 01 695 A1 | 7/2002 |
| DE | 103 36 386 A1 | 3/2004 |
| DE | 102 45 585 A1 | 4/2004 |
| DE | 103 32 758 A1 | 5/2004 |
| EP | 0 092 097 A1 | 10/1983 |
| EP | 0 253 409 A2 | 1/1988 |
| EP | 0 270 999 A1 | 6/1988 |
| EP | 0 312 191 A2 | 4/1989 |
| EP | 0 529 853 A2 | 3/1993 |
| EP | 0 648 732 A1 | 4/1995 |
| EP | 0 695 736 A1 | 2/1996 |
| EP | 0 778 255 A1 | 6/1997 |
| EP | 0 784 046 A1 | 7/1997 |
| EP | 0 792 867 A2 | 9/1997 |
| EP | 0 982 287 A1 | 3/2000 |
| EP | 0 982 288 A2 | 3/2000 |
| EP | 0 982 289 A2 | 3/2000 |
| EP | 0 990 636 A1 | 4/2000 |
| EP | 1 041 062 A2 | 10/2000 |
| EP | 1 070 700 A2 | 1/2001 |
| EP | 1 106 598 A2 | 6/2001 |
| EP | 1 125 912 A2 | 8/2001 |
| EP | 1 192 987 A1 | 4/2002 |

(Continued)

Primary Examiner—Yvonne Eyler
Assistant Examiner—M Louisa Lao
(74) Attorney, Agent, or Firm—Oblon, Spivak, McClelland, Maier & Neustadt, P.C.

(57) ABSTRACT

A process for rectificatively separating a liquid which comprises acrylic acid, methacrylic acid or a mixture thereof, and additionally comprises low molecular weight aldehydes and acetone.

10 Claims, No Drawings

FOREIGN PATENT DOCUMENTS

| | | |
|---|---|---|
| EP | 1 212 280 | 6/2002 |
| EP | 1 350 784 A1 | 10/2003 |
| GB | 1 346 737 | 2/1974 |
| JP | 7-10802 | 1/1995 |
| WO | WO 01/19769 A1 | 3/2001 |
| WO | WO 01/96270 A2 | 12/2001 |
| WO | WO 03/011804 A2 | 2/2003 |
| WO | WO 2005/035478 A2 | 4/2005 |

* cited by examiner

PROCESS FOR RECTIFICATIVELY SEPARATING A LIQUID COMPRISING ACRYLIC ACID AND/OR METHACRYLIC ACID

TITLE OF THE INVENTION

Process for rectificatively separating a liquid comprising acrylic acid and/or methacrylic acid

BACKGROUND OF THE INVENTION

1. Field of the Invention

The present invention relates to a process for rectificatively separating a liquid II whose content of acrylic acid and/or methacrylic acid, based on the total weight of the liquid II, is at least 10% by weight, and which, in addition to methacrylic acid and/or acrylic acid, comprises both acrolein and/or methacrolein and acetone in a total amount of not more than 5% by weight, based on the amount of acrylic acid and/or methacrylic acid present in the liquid II, with the proviso that the weight ratio of acrolein present in the liquid II to acetone present in the liquid II is different from 3.5, and which has been generated without adding acrolein or methacrolein as a pure substance to another liquid I comprising acrylic acid and/or methacrylic acid.

2. Description of the Background

Acrylic acid and methacrylic acid, either as such or in the form of their esters, are of significance especially for the preparation of polymers for a wide variety of applications, for example use as adhesives, use as water-superabsorbent materials, and have a high tendency to free-radically polymerize especially in the liquid phase. Safe storage of liquids comprising acrylic acid and/or methacrylic acid is possible at low temperatures only with addition of polymerization inhibitor. Acrylic acid and methacralic acid are obtainable by methods including partial heterogeneously catalyzed gas phase oxidation of precursor compounds such as alkanes, alkanols, alkenes and/or alkenals which comprise 3 or 4 carbon atoms (or from a mixture thereof). Acrylic acid is obtainable advantageously by partial heterogeneously catalyzed gas phase oxidation of propane, propene and/or acrolein. Methacrylic acid is obtainable advantageously by partial heterogeneously catalyzed gas phase oxidation of tert-butanol, isobutene, isobutane, isobutyraldehyde and/or methacrolein. However, conceivable starting compounds are also those from which the actual $C_3/C_4$ starting compounds is only formed as an intermediate during the partial heterogeneously catalyzed gas phase oxidation. An example is the methyl ether of tert-butanol.

The starting gases mentioned are generally diluted with inert gases such as nitrogen, $CO_2$, other saturated hydrocarbons, CO, noble gas (He, Ar, etc.) and/or steam, passed in a mixture with oxygen, at elevated temperatures (typically from 200 to 400 or to 450° C.) and, if appropriate, pressure elevated above standard pressure, over preferably transition metal mixed oxide catalysts (comprising, for example, Mo, Fe and Bi or Mo and V or Mo and P) and converted oxidatively to acrylic acid and/or methacrylic acid (cf. for example, DE-A 44 05 059, EP-A 253 409, EP-A 092 097, DE-A 44 31 949, EP-A 990 636, EP-A 1 106 598, EP-A 1 192 987, EP-A 529 853, EP-A 1 350 784, DE-A 198 55 913 and DE-A 101 01 695 and also the prior art cited in these documents).

In general, acrylic acid is prepared from $C_3$ precursors separately from the preparation of methacrylic acid which is prepared starting from $C_4$ precursors. When the starting material is a mixture of $C_3$ and $C_4$ precursors, acrylic acid and methacrylic acid can, though, also be prepared in a mixture by partial catalytic oxidation in the gas phase.

However, owing to numerous parallel and subsequent reactions proceeding in the course of the heterogeneously catalyzed partial gas phase oxidation and owing to the inert diluent gases also to be used and the impurities present in the crude alkanes, alkanols, alkenes and/or alkenals (cf., for example, DE-A 102 45 585, WO 01/96270 and WO 03/011804 (for example use of polymer-grade or of chemical-grade propylene)), not only acrylic acid and/or methacrylic acid are obtained in the heterogeneously catalyzed partial gas phase oxidation, but rather a reaction gas mixture which, in addition of acrylic acid and/or methacrylic acid and the inert diluent gases, comprises by-products from which the acrylic acid and/or methacrylic acid desired as the target product have to be removed.

Typically, the acrylic acid and/or methacrylic acid are removed from the reaction gas mixture of the heterogeneously catalyzed partial gas phase oxidation by initially converting the acrylic acid and/or methacrylic acid from the gas phase into the liquid phase in a basic removal.

This can be effected, for example, by subjecting the product gas mixture of the heterogeneously catalyzed partial gas phase oxidation to a condensation step which can be induced by direct and/or indirect cooling. Preference is given to performing the condensation step in a fractionating manner (cf., for example, DE-A 199 24 532, DE-A 199 24 533, DE-A 197 40 253, DE-A 196 27 847 and DE-A 103 32 758).

Alternatively, the acrylic acid and/or methacrylic acid can also be converted to the condensed phase by absorbing them out of the reaction mixture of the heterogeneously catalyzed partial gas phase oxidation into a suitable absorbent (cf., for example, US 2004/0242826, DE-A 196 06 877, DE-A 196 31 645, EP-A 982 289, EP-A 982 288, EP-A 982 287, EP-A 792 867, EP-A 784 046, DE-A 103 36 386, DE-A 43 08 087, DE-A 21 36 396, EP-A 648 732 (especially the working example), EP-A 1 125 912, EP-A 1 212 280).

Useful absorbents are, for example, water, aqueous solutions and organic solvents. Preferred organic absorbents are those whose boiling point under standard conditions (1 bar) is above the boiling point of acrylic acid and/or methacrylic acid and which are preferably comparatively hydrophobic in order to very substantially prevent coabsorption of water of reaction.

Such suitable organic absorbents are, for example, a mixture of from 70 to 75% by weight of diphenyl ether and from 25 to 30% by weight of diphenyl and also mixtures of from 0.1 to 25% by weight of o-dimethyl phthalate and from 75 to 99.9% by weight of an aforementioned diphenyl ether/diphenyl mixture (cf., for example, DE-A 43 08 087 and DE-A 21 36 396).

It will be appreciated that absorption and condensation may also be employed in combination, as described, for example, by EP-A 784 046 and by DE-A 44 36 243.

Depending on the aim, it is possible to remove low-boiling secondary components from the condensate or absorbate by means of desorption and/or stripping by means of gases such as nitrogen or air. Subsequently, the acrylic acid and/or methacrylic acid can be removed in any purity from the remaining condensed phase via rectificative separating sequences. It will be appreciated that the rectificative removal of the acrylic acid and/or methacrylic acid may also be undertaken directly out of the absorbate or condensate. When the conversion from the gas phase into the condensed phase is carried out in such a way that it comprises the acrylic acid and/or methacrylic acid in comparatively dilute form (for example only to an extent of 30% by weight, or only to an extent of 20% by weight, or only to an extent of 10% by weight), the prior art also recommends enriching the acrylic acid and/or methacrylic acid out of the directly obtained condensed phase into a suitable extractant by extraction by means of said extractant (before or after a desorption and/or stripping) (cf., for example, patent 54 354 of the German Democratic Republic and EP-A 312 191) and subsequently undertaking the rectificative removal of acrylic acid and/or methacrylic acid starting from the extract.

When an aqueous phase has been used as the absorbent, a first rectificative separation step may also consist in removing water from the condensed phase with the aid of an azeotropic entraining agent (cf., for example, US 2004/ 0242286, EP-A 695 736, EP-A 778 255, EP-A 1 041 062, EP-A 1 070 700).

A disadvantage of the procedures described is that the reaction gas mixture of the heterogeneously catalyzed gas phase partial oxidation essentially unavoidably still comprises residues of the precursor aldehyde of acrylic acid and/or methacrylic acid, i.e. acrolein and/or methacrolein. This can be attributed to the fact that the heterogeneously catalyzed catalytic oxidative preparation of acrylic acid and/or methacrylic acid in the gas phase always proceeds via the corresponding precursor aldehyde as the precursor (cf., for example, JP-A 7-10802).

This is disadvantageous in that, according to DE-A 195 39 295 for example, the polymerization tendency both of acrylic acid and of methacrylic acid is significantly increased in the presence even of the smallest amounts of their precursor aldehyde (in the ppm range). This is disadvantageous in particular because the above-described condensed phases comprising acrylic acid and/or methacrylic acid normally in general also comprise small amounts of the corresponding precursor aldehyde (depending on the contamination of the raw material used for the partial oxidation, both precursor aldehydes, i.e. acrolein and methacrolein, may be present both in the case of acrylic acid and in the case of methacrylic acid), which is one cause of the fact that, under the thermal stress of a rectification in particular, the rectificative separation of liquids which, in addition to methacrylic acid and/or acrylic acid, also comprise acrolein and/or methacrolein, has to be interrupted from time to time owing to undesired polymer formation.

As a countermeasure, the prior art recommends carrying out both the conditions of the heterogeneously catalyzed gas phase partial oxidation and the conversion of the acrylic acid and/or methacrylic acid from the gas phase into the liquid phase and the treatment of the latter in advance of a subsequent rectificative separation in such a way that the liquid which is to be treated rectificatively and comprises acrylic acid and/or methacrylic acid comprises a minimum amount of acrolein and/or methacrolein and a minimum amount of other aldehydic by-products, for example formaldehyde, glyoxal, acetaldehyde, propionaldehyde, n-butyraldehyde, isobutyraldehyde, furfural, benzaldehyde and crotonaldehyde (all of which equally have polymerization-promoting action; however, the precursor aldehydes (also owing to their physical properties) are of the greatest significance with regard to amount and effect). Influencing parameters to be selected suitably in this regard are the selection of the multimetal oxide catalysts, the selection of the raw material, the selection of the reaction temperature, the selection of the conversion, the selection of the degree of dilution in the reaction gas mixture, the selection of the absorbent, the selection of the absorption conditions, etc.

All of the aforementioned measures are afflicted with disadvantages. In particular, pure raw materials are comparatively expensive.

High conversions of the aldehydic precursor compound to the acrylic acid and/or methacrylic acid target products are typically necessarily associated with an increased proportion of full combustion to $CO_2$ and $H_2O$. Reduction in the aldehyde content brought about by desorption and/or by means of low boiling stripping normally causes losses of acrylic acid and/or methacrylic acid. Highly selective multimetal oxide catalysts are generally comparatively costly and inconvenient in their preparation, etc.

Alternatively, the prior art recommends chemically binding the aldehydic secondary components by a rectificative pretreatment by means of compounds which have an amine group (cf., for example, EP-A 312 191, DE-A 22 07 184, DE-A 195 39 295, EP-A 270 999, DE-A 196 34 614, etc.).

However, a disadvantage of this procedure is that it requires an additional material. EP-A 1 041 062 for the first time addresses the role of a further secondary component which is unavoidably also formed in the catalytic oxidative preparation in the gas phase of acrylic acid from $C_3$ precursor compounds (in particular propylene, acrolein and/or propane) and in the catalytic oxidative preparation in the gas phase of methacrylic acid from $C_4$ precursor compounds (in particular isobutene, methacrolein, tert-butanol, isobutyraldehyde, isobutane and/or the methyl ether or tert-butanol). This secondary component is acetone.

According to the teaching of EP-A 1 041 062 and the accompanying opposition file, the acetone is postulated to have the same action as the precursor aldehydes acrolein and methacrolein. In other words, it is assumed that presence of acetone undesirably promotes the tendency of acrylic acid and/or methacrylic acid to free-radically polymerize in the same way as presence of acrolein and/or methacrolein in the condensed phase. In this regard, even synergistic interaction of acetone and the precursor aldehydes is assumed.

SUMMARY OF THE INVENTION

However, EP-A 1 041 062 does not comprise correspondingly meaningful experimental investigations. It is merely recommended to very substantially lower the total amount of acetone and $C_2$- to $C_4$-adehydes (in particular acrolein and methacrolein) in advance of a rectificative separation and the action of such a combined lowering is verified.

In extended in-house investigations, it has now been found that, surprisingly, acetone, especially in the presence of the precursor aldehydes, in the condensed phase, does not only have a promoting action on the tendency of acrylic acid and/or methacrylic acid to free-radically polymerize. Instead, a polymerization-inhibiting action can be ascribed to acetone in the above context.

Accordingly, in accordance with the invention, an improved process has been found for rectificatively separating a liquid II whose content of acrylic acid and/or methacrylic acid, based on the total weight of the liquids II, is at least 10% by weight, and which, in addition to methacrylic acid and/or acrylic acid, comprises both acrolein and/or methacrolein and acetone in a total amount of not more than 5% by weight, based on the amount of acrylic acid and/or methacrylic acid present in the liquids II, with the proviso that the weight ratio of acrolein present in the liquid II to acetone present in the liquid II is different from 3.5, and which has been generated without adding acrolein or methacrolein as a pure substance to another liquid I comprising acrylic acid and/or methacrylic acid, which comprises conducting the liquid II into a rectification column with the proviso that it comprises, based on the total amount of acrolein and methacrolein present in the liquids II, at least 10% by weight of acetone.

DETAILED DESCRIPTION OF THE PREFERRED EMBODIMENTS

Preferably in accordance with the invention, the liquid II fed to the rectification column, based on the total amount of acrolein and methacrolein present therein, comprises at least 15% by weight, advantageously at least 20% by weight, more advantageously at least 25% by weight, better at least 30% by weight, even better at least 35% by weight, with preference at least 40% by weight, more preferably at least 45% by weight and most preferably at least 50% by weight, of acetone.

In other words, the liquid II fed to the rectification column may, in the process according to the invention, based on the total amount of acrolein and methacrolein present therein, comprise at least 55% by weight, or at least 60% by weight, or at least 65% by weight, or at least 70% by weight, or at least 75% by weight, or at least 80% by weight, or at least 85% by weight, or at least 90% by weight, or at least 95% by weight, or at least 100% by weight or more (for example at least 110% by weight, or at least 120% by weight, or at least 130% by weight, or at least 140% by weight, or at least 150% by weight, or at least 170% by weight, or at least 200% by weight, or at least 300% by weight), of acetone.

In general, the liquid II fed to the rectification column in the process according to the invention, based on the total amount of acrolein and methacrolein present therein, will not comprise more than 1000% by weight, frequently not more than 900% by weight, in many cases not more than 800% by weight, often not more than 700% by weight, in some cases not more than 600% by weight, sometimes not more than 500% by weight and under some circumstances not more than 400% by weight, of acetone.

This can be attributed not least to the fact that acetone is not formed as a by-product in large amounts in the relevant partial oxidations of $C_3$ and/or $C_4$ precursor compounds of acrylic acid and/or methacrylic acid. For a realization of the process according to the invention without the addition of external acetone (i.e. not stemming from the partial heterogeneously catalyzed gas phase oxidation itself which leads to the desired acrylic acid and/or methacrylic acid) into the liquids II, a particularly careful selection of the boundary conditions both for the partial gas phase oxidation and for the conversion of the acrylic acid/or methacrylic acid present in the product gas mixture thereof to the condensed phase is required.

A relative enrichment of the acetone can preferably be achieved by a skillful selection of the multimetal oxide catalysts for the partial oxidation of acrylic acid and/or methacrylic acid precursor compounds which is appropriately carried out in two stages advantageously starting from propylene or isobutene. A few exploratory experiments for an appropriate selection are sufficient in this regard for the person skilled in the art. Elevated reaction temperatures generally promote acetone formation. The same applies for elevated contents of the particular precursor compound in the starting reaction gas mixture and to a low specific heat of the inert diluent gases employed. It is also favorable to select the hourly space velocity on the catalyst bed (advantageously in accordance with the invention a fixed catalyst bed) of the particular precursor compound at $\geq$120 l (STP)/l·h, or $\geq$130 l (STP)/l·h, or $\geq$140 l (STP)/l·h, or $\geq$150 l (STP)/l·h, or $\geq$160 l (STP)/l·h. In general, the aforementioned hourly space velocity on the fixed catalyst bed will be $\leq$300 l (STP)/l·h, frequently $\leq$250 l (STP)/l·h and in many cases $\leq$200 l (STP)/l·h.

When propylene is the starting material used to prepare acrylic acid, multimetal oxide catalysts comprising preferably Mo, Bi and Fe will be used in the first reaction stage (propylene to acrolein). Useful such catalysts are in particular those of EP-A 015 565, EP-A 575 897, DE-A 197 46 210 and DE-A 198 55 913. These multimetal oxide catalysts are equally suitable for the first oxidation stage of a catalytic oxidative preparation in the gas phase of methacrolein from isobutene. In the second oxidation stage (acrolein to acrylic acid), multimetal oxide catalysts comprising Mo and V will be used advantageously. Useful such catalysts are in particular those of DE-A 100 46 925, DE-A 198 15 281, DE-A 43 35 973, EP-A 714 700, EP-A 668 104, DE-A 197 36 105, DE-A 197 40 493 and DE-A 195 28 646.

Appropriately in accordance with the invention, the acrolein conversion in the second oxidation stage (acrolein to acrylic acid) is from 99.0 to 99.9 mol %, preferably from 99.3 to 99.9 mol % and more preferably from 99.6 to 99.9 mol %.

The aforementioned maximum values are achievable, for example, when the second reaction stage comprises at least one postreactor according to DE-A 10 2004 021 764 or DE-A 10 2004 021 763. Alternatively, process variants according to the prior art cited in these documents may be employed.

The propylene conversion in the first oxidation stage is advantageously selected at $\geq$94 mol %, and $\leq$99 mol %. Multimetal oxide catalysts (which preferably comprise Mo and P) for the second oxidation stage "methacrolein to methacrylic acid" may be taken from DE-A 25 26 238, EP-A 092 097, EP-A 058 927, DE-A 41 32 263, DE-A 41 32 684 and DE-A 40 22 212.

It is also possible to generate liquids II suitable for processes according to the invention by using the organic absorbent already mentioned in this document in order to convert the acrylic acid and/or methacrylic acid from the gas phase of the reaction gas mixture of the partial oxidation into the condensed phase. However, preferably in accordance with the invention, this conversion into the condensed phase is effected by fractionally condensing the reaction gas mixture (ascending into itself in separating columns comprising separating internals) and/or by absorption into water or aqueous solutions (preferably in countercurrent).

This is because acetone has a particularly high affinity for water (be it the condensed water of reaction flowing in countercurrent and/or external water or external aqueous solution introduced for absorption purposes and flowing in countercurrent (it should consist at least to an extent of 80% by weight, preferably to an extent of at least 90% by weight and more preferably to an extent of at least 95% by weight, of water)). Small amounts of aqueous absorbent are preferred in accordance with the invention because they intensify the relative enrichment of acetone.

Amounts of aqueous absorbent favorable in accordance with the invention may, for example, be from 5 to 10 liters per $m^3$ (STP) of reaction gas mixture.

For example, suitable aqueous absorbents are aqueous solutions (which may be taken from the process) which comprise:

from 0.1 to 5% by weight of acrylic acid,
from 0.1 to 10% by weight of acetic acid and
from 80 to 99.8% by weight of water.

In a relative enrichment of acetone, it is also advantageous in accordance with the invention when the aqueous phase flowing in countercurrent to the reaction gas mixture ascending within the separating column comprising separating internals has, at the top thereof, a temperature of from 60 to 90° C. Temperatures below this are less preferred in accordance with the invention in the sense of relative enrichment of acetone in the absorbate.

A further relative enrichment of acetone can be brought about by subjecting the resulting aqueous absorbate to a desorption and/or stripping with air, nitrogen and/or another inert gas under suitable conditions. It is advantageous in this case when both the bottom and the top temperature in the separating column comprising separating internals which is used is not too high. Favorably in accordance with the invention, the aforementioned temperatures are from 50 to 75° C. It is also advantageous in the inventive sense when the top pressure employed is not selected at too low a level. Preferred top pressures are from 600 mbar up to 1 bar.

Should the relative enrichment of acetone achieved in the way described not be sufficient (a further means of enrichment consists in prerectification at low temperatures and not excessively low pressures), acetone can additionally be added to the liquid to be treated in accordance with the invention. This measure is comparatively innocuous in that a removal of the acetone desired in the further course of the removal of acrylic acid and/or methacrylic acid is achievable effortlessly by rectification.

In other words, the number of separating steps required to achieve glacial acrylic acid and/or glacial methacrylic acid is not increased in the process according to the invention (the aforementioned glacial acids normally comprise $\geq 99.8\%$ by weight of acrylic and/or methacrylic acid).

An essential feature of the process according to the invention is that it is applicable in particular to liquids II which have been generated without adding acrolein and acetone as a pure substance (purity normally $\geq 99.8\%$ by weight) to glacial acrylic acid.

Furthermore, the process according to the invention is applicable to liquids II which have been generated without adding methacrolein and acetone as a pure substance to glacial methacrylic acid.

In particular, the process according to the invention is applicable to liquids II even when the ratio of the total weight of acrolein and methacrolein present therein to the weight of acetone is not from 0.95 to 1.07.

The process according to the invention is also applicable to liquids II in which the weight ratio of acrolein present to acetaldehyde is not 10:1 and not 12:1 or not from 10:1 up to 12:1. This is especially true when the weight ratio of acrolein present to acetone present in the liquid II is not simultaneously (or not only) 5:1 or 3.5:1 or not simultaneously (or not only) from 3.5:1 to 5:1.

The process according to the invention is applicable in particular to liquids II whose content of acrylic acid and/or methacrylic acid, based on the total weight of the liquids II, is $\geq 20\%$ by weight, or $\geq 30\%$ by weight, or $\geq 40\%$ by weight, or $\geq 50\%$ by weight, or $\geq 60\%$ by weight, or $\geq 70\%$ by weight, or $\geq 80\%$ by weight, or $\geq 90\%$ by weight, or $\geq 95\%$ by weight, or $\geq 98\%$ by weight.

In general, the content in the liquids II to be treated in accordance with the invention of acrylic acid and/or methacrylic acid will be $\leq 99\%$ by weight.

In other words, the process according to the invention is suitable, for example, for liquids II which comprise from 20 to 65% by weight, or from or from 30 to 65% by weight, or from 40 to 65% by weight, or from 50 to 65% by weight, based on the total weight of the liquids II, of acrylic acid and/or methacrylic acid.

However, it is also suitable for liquids II which comprise from 70 to 95% by weight, or from 72 to 90% by weight, or from 75 to 85% by weight, based on the total weight of the liquids II, of acrylic acid and/or methacrylic acid.

In particular, the process according to the invention is suitable for liquids II (which comprise water) whose content of water, based on the total weight of the liquids II, is less or more than 30% by weight (or equals 30% by weight). In other words, the process according to the invention is applicable to liquids II whose water content, as described above, is from 5 to 28% by weight, or from 10 to 25% by weight, or from 15 to 20% by weight. However, it is also applicable to liquids II whose water content, as described above, is from 32 to 85% by weight, or from 35 to 80% by weight, or from 40 to 75% by weight, or from 45 to 70% by weight, or from 50 to 65% by weight, or from 55 to 60% by weight. Instead of water, the aforementioned liquids II may also comprise mixtures of from 70 to 75% by weight of diphenyl ether and from 25 to 30% by weight of diphenyl. It will be appreciated that such water representatives may also be mixtures of from 70 to 75% by weight of diphenyl ether and from 25 to 30% by weight of diphenyl and also, based on these mixtures, from 0.1 to 25% by weight of dimethyl phthalate.

Further useful water representatives may also be mixtures of water and an azeotropic entraining agent, for example heptane, dimethylcyclohexane, ethylcyclohexane, toluene, ethylbenzene, chlorobenzene, xylene or mixtures of these entraining agents.

In general, the liquid II to be treated in accordance with the invention, based on the amount of acrylic acid and/or methacrylic acid present in the liquids II, will comprise at least 10 ppm by weight of acrolein and/or methacrolein. Frequently, the aforementioned content of acrolein and/or methacrolein in the process according to the invention will be at least 20 ppm by weight, or at least 30 ppm by weight, or at least 40 ppm by weight, or at least 50 ppm by weight, or at least 60 ppm by weight, or at least 70 ppm by weight, or at least 80 ppm by weight, or at least 90 ppm by weight, or at least 100 ppm by weight.

In many cases, the aforementioned content of acrolein and/or methacrolein will be at least 150 ppm by weight, or at least 250 ppm by weight, or at least 300 ppm by weight, or at least 400 ppm by weight, or at least 500 ppm by weight. In general, the aforementioned content of acrolein and/or methacrolein in the liquid II to be treated in accordance with the invention will, however, be $\leq 20\,000$ ppm by weight, in many cases $\leq 15\,000$ ppm by weight, frequently $\leq 10\,000$ ppm by weight, and often even $\leq 7500$ ppm by weight or $\leq 5000$ ppm by weight.

In other words, the total content in the liquid II to be treated in accordance with the invention of acrolein and methacrolein and also acetone will, based on its total weight, in many cases be from $\geq 10$ ppm by weight to $\leq 4\%$ by weight, or from $\geq 20$ ppm by weight to $\leq 3\%$ by weight, or from $\geq 30$ ppm by weight to $\leq 2.5\%$ by weight, or from $\geq 40$ ppm by weight to $\geq 2\%$ by weight, or from $\geq 50$ ppm by weight to $\leq 1.5\%$ by weight, or from $\geq 75$ ppm by weight to $\leq 1\%$ by weight, or from $\geq 100$ ppm by weight to $\leq 0.5\%$ by weight.

In addition to acrolein and/or methacrolein, the liquid II to be treated in accordance with the invention may additionally comprise other aldehydes, for example benzaldehyde and furfurals. Based on the amount of acrylic acid and/or methacrylic acid present in the liquids II, the content in the liquid II of benzaldehyde and/or furfurals (furfural-2 and/or furfural-3) may in each case be from 10 ppm by weight to 10 000 ppm by weight, or from 20 ppm by weight to 5000 ppm by weight, or from 50 to 3000 ppm by weight.

The liquid II in the process according to the invention may also additionally comprise lower aldehydes such as formaldehyde, glyoxal, acetaldehyde, propionaldehyde, n-butyraldehyde, isobutyraldehyde and crotonaldehyde. Their proportions may be of a comparable order of magnitude to those mentioned above.

Advantageously, the liquid II fed to the reaction column in the process according to the invention, based on the total amount of aldehydes present therein, comprises at least 10% by weight, or at least 15% by weight, advantageously at least 20% by weight, more advantageously at least 25% by weight, better at least 30% by weight, even better at least 35% by weight, with preference at least 40% by weight, more preferably at least 45% by weight and most preferably at least 50% by weight, of acetone. Typically, the aforementioned acetone content will, however, not be more than 500% by weight. At the same time, the aldehyde content may be lowered in a controlled manner, for example, by adding active ingredients to the liquid II which selectively chemically bind the aldehydes.

It will be appreciated that all process stages addressed in this document in which acrylic acid and/or methacrylic acid is present in the liquid phase are carried out in the presence of polymerization inhibitors. Useful such inhibitors are in particular hydroquinone, phenothiazine (PTZ), hydroquinone monomethyl ether (MEHQ) and N-oxyl radicals (cf. US-A 2004/0242826).

Among the latter, preference is given in particular to 4-hydroxy-2,2,6,6-tetramethylpiperidine N-oxyl and 2,2,6,6-tetramethylpiperidine N-oxyl (or the mixture thereof).

The aforementioned polymerization inhibitors may each be used alone or else in a wide variety of mixtures. Typically, they are used in a total amount of from 100 to 5000 ppm by weight, preferably from 200 to 1000 ppm by weight, based on the weight of the liquid phase comprising acrylic acid and/or methacrylic acid. It will be appreciated that the aforementioned polymerization inhibitors may also be used as a constituent of other polymerization inhibitor systems. In general, in the inventive rectification, molecular oxygen is also used as a polymerization inhibitor. This is possible in a simple manner by conducting an air stream through the rectification column.

In addition to the liquids II, the reflux liquid in the rectification column may also be polymerization-inhibited in the process according to the invention.

The acrylic acid and/or methacrylic acid may be enriched in the inventive rectificative separation of liquids II either at the top or in the bottom of the rectification column. It will be appreciated that fractions comprising enriched acrylic acid and/or methacrylic acid may also be withdrawn in the upper, lower or middle section of the rectification column.

The separating internals normally present in the rectification column in the process according to the invention fulfill the purpose in the process according to the invention of increasing the surface area for the heat and oxygen transfer which brings about the separation in the separating column. Useful such internals are, for example, structured packings, random packings and/or mass transfer trays. The latter may, for example, be sieve trays (forced sieve trays or dual-flow (trickle sieve trays) trays) and/or bubble-cap trays.

Mass transfer trays on which equilibrium exists between descending liquid and ascending vapor are referred to as theoretical plates. This term can also be applied to all other separating internals suitable for countercurrent rectifications (for example structured packings and beds of random packings).

In this document, reference is therefore made for convenience quite generally to theoretical plates. A theoretical plate is defined as being that unit of space which brings about enrichment in accordance with the thermodynamic equilibrium.

The feed of the liquid II into the rectification column may, based on the total number of theoretical plates (and viewed from the bottom upward), may either be in the lower third or in the upper third of the rectification column. On a corresponding basis, it may also be below or above the middle of the rectification column. It will be appreciated that the feed of the liquid II into the rectification column may also be at the top of the column below the top product withdrawal.

Appropriately in accordance with the invention, at least two, or at least four, or at least six, or at least eight, or at least 10, or at least 12, theoretical plates are disposed above the feed point of the liquid II into the rectification column in the process according to the invention.

In principle, the feed of the liquid II into the rectification column in the process according to the invention may also be directly into the bottom of the rectification column. The reflux ratio in the process according to the invention may vary within wide ranges. It may, for example, be 2:1 (double reflux relative to the amount withdrawn) or more or less.

Preference is given to carrying out the process according to the invention under reduced pressure. Top pressures particularly suitable in accordance with the invention are $\leq 500$ mbar, more preferably from 10 to 500 mbar, frequently from 10 to 200 mbar and preferably from 10 to 190 or to 150 mbar. The pressure drop over the rectification column in the process according to the invention is advantageously from 300 to 100 mbar, or from 250 to 150 mbar.

The temperature in the bottom of the rectification column in the process according to the invention is appropriately from 50 to 230° C., preferably from 70 to 210° C., or from 90 to 190° C. or from 110 to 170° C.

In the process according to the invention, a liquid II at the feed point Z into the rectification column shall be understood to mean a stream which is present as a condensed phase to an extent of more than 80%, preferably to an extent of more than 85%, or to an extent of more than 90%, or to an extent of more than 95%, or to an extent of more than 99%, of its total volume.

Otherwise, the process according to the invention may be carried out, for example, like the rectificative processes described in the documents DE-A 103 47 664 and DE-A 103 00 816. Acrylic acid and/or methacrylic acid removed in the process according to the invention may, in processes for preparing polymers which follow the process according to the invention, be free-radically polymerized to such polymers.

EXAMPLES

A) Four indistinguishable samples of in each case 0.5 ml were freshly prepared (distillation, then freezing), whose content of acrylic acid was >99.8% by weight and whose aldehyde/ketone content was <10 ppm by weight. Each of the samples was polymerization-inhibited by adding 25 ppm by weight of phenothiazine. By addition of acetone and/or acrolein, the following contents of the individual samples were then established:

Sample 1: no addition;
Sample 2: 1000 ppm by weight of acrolein;
Sample 3: 10 000 ppm by weight of acrolein;
Sample 4: 1000 ppm by weight of acrolein and 1000 ppm by weight of acetone.

Under an air atmosphere, each of the samples was transferred into a 1.8 ml glass ampule. Immediately after completion, the ampules were stored with rotation in a forced-air drying cabinet at 120° C. in order to ensure full mixing.

The time T up to full polymerization of the particular sample was recorded visually.

The experimental series was repeated three times and the following T value [in minutes] was obtained:

|  | Experiment 1 | Experiment 2 | Experiment 3 | Mean |
|---|---|---|---|---|
| Sample 1 | 479 | 483 | 480 | 481 |
| Sample 2 | 299 | 283 | 294 | 292 |
| Sample 3 | 111 | 111 | 105 | 109 |
| Sample 4 | 323 | 321 | 327 | 324 |

B) In a corresponding manner to A), 4 indistinguishable samples of in each case 0.5 ml were freshly prepared, whose content of methacrylic acid was >99.8% by weight and whose aldehyde/ketone content was >10 ppm by weight. Each of the 4 samples was polymerization-inhibited by adding 10 ppm by weight of phenothiazine. By addition of acetone and/or methacrolein, the following contents of the individual samples were established:
Sample 1: no addition;
Sample 2: 10 000 ppm by weight of methacrolein;
Sample 3: 400 ppm by weight of acetone;
Sample 4: 1000 ppm by weight of methacrolein+1000 ppm by weight of acetone.

As described under A), the time T (in minutes) up to complete polymerization of the particular sample was determined. The experimental series was likewise repeated 3 times and the following T values [in minutes] were obtained:

|  | Experiment 1 | Experiment 2 | Experiment 3 | Mean |
|---|---|---|---|---|
| Sample 1 | 239 | 263 | 269 | 257 |
| Sample 2 | 190 | 200 | 200 | 197 |
| Sample 3 | 288 | 301 | 319 | 303 |
| Sample 4 | 288 | 288 | 310 | 295 |

C) The following rectification experiments were carried out:
I. Top metering
The rectification apparatus used comprised:
a three-neck flask having a capacity of 250 ml;
a Vigreux column of length 32 cm which was thermally insulated against the environment for a length of 21 cm;
an oil bath for heating the three-neck flask;
a needle valve with feed capillary for the purpose of top metering;
a capillary projecting into the liquid phase in the three-neck flask;
a thermoelement for determining the top temperature and a thermometer for determining the bottom temperature.

As in A), 100 g of acrylic acid having an acrylic acid content of >99.8% by weight and an aldehyde/ketone content of <10 ppm by weight were freshly prepared (distillation; then freezing) and subsequently admixed with 100 ppm by weight of phenothiazine (PTZ) and initially charged in the three-neck flask.

A further 60 g of the same acrylic acid admixed with 100 ppm by weight of phenothiazine were doped with different amounts of acrolein, acetone and/or acetaldehyde.

At a bath temperature of 100° C., a temperature of 87° C. was achieved in the three-neck flask. When a reduced pressure of 133 mbar was applied, the initially charged acrylic acid was distilled at a top temperature of 83° C. (temperature of the gas phase). A reflux ratio of 2:1 was established (double reflux relative to the amount withdrawn). The amount of acrylic acid withdrawn was compensated by top metering with the doped acrylic acid.

The rectification was operated continuously over 60 min in each case. Subsequently, the amount of polymer formed in each case was weighed. Polymer formation was detected in the column bottom and at the top of the column.

As a function of the doping used, the results listed in the Table 1 which follows were obtained:

TABLE 1

| Doping [ppm by weight] | | | Amount of polymer [mg] | |
|---|---|---|---|---|
| acrolein | acetone | acetaldehyde | at the top | in the bottom |
| 0 | 0 | 0 | 100 | <20 |
| 500 | 0 | 0 | 290 | <30 |
| 1000 | 0 | 0 | 400 | <20 |
| 0 | 1000 | 0 | 80 | <20 |
| 1000 | 1000 | 0 | 300 | <20 |
| 1000 | 2000 | 0 | 80 | <30 |
| 500 | 0 | 500 | 270 | 150 |
| 500 | 1000 | 500 | 110 | 55 |

II. Metering in the middle of the column
The experiment according to I. was repeated, except that the feed capillary was conducted to the middle of the column.

As a function of the doping used, the results listed in the Table 2 which follows were obtained:

TABLE 2

| Doping [ppm by weight] | | Amount of polymer [mg] | |
|---|---|---|---|
| acrolein | acetone | at the top | in the bottom |
| 0 | 0 | 150 | <30 |
| 1000 | 0 | 710 | <25 |
| 0 | 1000 | 110 | <25 |
| 1000 | 1000 | 360 | <25 |
| 1000 | 2000 | 310 | <25 |

III. Doped initial charge in the bottom
The experiment according to I. was repeated. In contrast to I., the initial charge was also doped.

As a function of the initial charge and/or top feed doping employed, the results listed in the Table 3 which follows were obtained:

TABLE 3

| Doping [ppm by weight] | | | | Amount of polymer [mg] | |
|---|---|---|---|---|---|
| Acrolein (top) | Acetone (top) | Acrolein (initial charge) | Acetone (initial charge) | at the top | in the bottom |
| 0 | 0 | 1000 | 0 | 240 | <20 |
| 1000 | 0 | 1000 | 0 | 190 | 420 |
| 0 | 0 | 1000 | 1000 | 110 | <25 |

TABLE 3-continued

| Doping [ppm by weight] | | | | Amount of polymer [mg] | |
|---|---|---|---|---|---|
| Acrolein (top) | Acetone (top) | Acrolein (initial charge) | Acetone (initial charge) | at the top | in the bottom |
| 0 | 0 | 0 | 1000 | 105 | <25 |
| 1000 | 1000 | 1000 | 1000 | 150 | 100 |

U.S. Provisional Patent Application No. 60/675,087, filed on Apr. 27, 2005, is incorporated into the present application by literature reference.

With regard to the abovementioned teachings, numerous alterations and deviations from the present invention are possible.

It can therefore be assumed that the invention, within the scope of the appended claims, can be performed in a different way from that specifically described herein.

What is claimed is:

1. A process for rectificatively separating a liquid II whose content of acrylic acid and/or methacrylic acid, based on the total weight of the liquid II, is at least 10% by weight, and which, in addition to methacrylic acid and/or acrylic acid, comprises both acrolein and/or methacrolein and acetone in a total amount of not more than 5% by weight, based on the amount of acrylic acid and/or methacrylic acid present in the liquid II, with the proviso that the weight ratio of acrolein present in the liquid II to acetone present in the liquid II is different from 3.5, and which has been generated without adding acrolein or methacrolein as a pure substance to a liquid I comprising acrylic acid and/or methacrylic acid, which comprises:

conducting the liquid II into a rectification column where liquid II comprises, based on the total amount of acrolein and methacrolein present in the liquid II, at least 10% by weight of acetone, whose presence has an inhibitory effect on the polymerization of acrylic acid and/or methacrylic acid in liquid II.

2. The process according to claim 1, wherein the liquid II conducted into the rectification column, based on the total amount of acrolein and methacrolein present in liquid II, comprises at least 20% by weight of acetone.

3. The process according to claim 1, wherein the liquid II conducted into the rectification column, based on the total amount of acrolein and methacrolein present in the liquid II, comprises at least 30% by weight of acetone.

4. The process according to any of claims 1 to 3, wherein the content in the liquid II of acrylic acid and/or methacrylic acid ranges from 20 to 99% by weight.

5. The process according to any of claims 1 to 3, wherein the content in the liquid II of acrylic acid and/or methacrylic acid ranges from 20 to 65% by weight or from 70 to 95% by weight.

6. The process according to claim 1, wherein the liquid II comprises water.

7. The process according to claim 1, wherein the liquid II comprises more than 30% by weight of water.

8. The process according to claim 1, wherein the liquid II comprises from 5 to 30% by weight of water.

9. The process according to claim 1, wherein the liquid II comprises, as polymerization inhibitor, at least one added N-oxyl radical.

10. The process according to claim 1, wherein the process for rectificative separation is followed by a process for preparing polymers in which rectificatively removed acrylic acid and/or methacrylic acid is free-radically polymerized to such polymers.

* * * * *